United States Patent
Kan (10) Patent No.: US 10,369,707 B2
(45) Date of Patent: Aug. 6, 2019

(54) JOINT OF ROBOT ARM AND SURGICAL INSTRUMENT

(71) Applicant: KAWASAKI JUKOGYO KABUSHIKI KAISHA, Kobe-shi, Hyogo (JP)

(72) Inventor: Kazutoshi Kan, Kobe (JP)

(73) Assignee: KAWASAKI JUKOGYO KABUSHIKI KAISHA, Kobe-shi (JP)

( * ) Notice: Subject to any disclaimer, the term of this patent is extended or adjusted under 35 U.S.C. 154(b) by 0 days.

(21) Appl. No.: 15/742,900

(22) PCT Filed: Jul. 9, 2015

(86) PCT No.: PCT/JP2015/003484
§ 371 (c)(1),
(2) Date: Jan. 9, 2018

(87) PCT Pub. No.: WO2017/006373
PCT Pub. Date: Jan. 12, 2017

(65) Prior Publication Data
US 2018/0200895 A1 Jul. 19, 2018

(51) Int. Cl.
*B25J 17/00* (2006.01)
*B25J 17/02* (2006.01)
(Continued)

(52) U.S. Cl.
CPC ............ *B25J 17/025* (2013.01); *A61B 34/30* (2016.02); *B25J 9/104* (2013.01);
(Continued)

(58) Field of Classification Search
CPC ......... B25J 9/104; B25J 17/025; B25J 17/00; A61B 2034/306; A61B 34/30; A61B 2034/715
(Continued)

(56) References Cited

U.S. PATENT DOCUMENTS

2006/0178560 A1* 8/2006 Saadat ................. A61B 1/0055
600/114
2012/0289946 A1* 11/2012 Steger .................... A61B 17/29
606/1
2014/0005681 A1 1/2014 Gee et al.

FOREIGN PATENT DOCUMENTS

EP 2 467 083 B1 2/2015
EP 1 585 425 B1 8/2016
(Continued)

OTHER PUBLICATIONS

Sep. 29, 2015 Search Report issued in International Patent Application No. PCT/JP2015/003484.
(Continued)

*Primary Examiner* — Jake Cook
(74) *Attorney, Agent, or Firm* — Oliff PLC (57) ABSTRACT

Joint coupling links of robot arm to each other includes: plurality of plate-shaped segments lined up in plate thickness direction; and operating wires extending through plurality of segments in plate thickness direction. Groove extending in second direction and having partially circular cross section is provided at first-direction middle portion of main surface out of two main surfaces of adjacent segments, two main surfaces facing each other in plate thickness direction. Projection extending in second direction and having partially circular cross section is provided at first-direction middle portion of main surface. Curvature of projection is larger than curvature of groove. Projection is fitted in groove, and bottom portion of groove and top portion of projection contact each other. Dimension of projection in plate thickness direction is larger than dimension of groove in plate thickness direction and smaller than length of line connecting bottom portion of groove and edge portion of groove.

7 Claims, 8 Drawing Sheets

(51) Int. Cl.
*B25J 18/00* (2006.01)
*A61B 34/30* (2016.01)
*B25J 9/10* (2006.01)
*A61B 34/00* (2016.01)

(52) U.S. Cl.
CPC ... *A61B 2034/306* (2016.02); *A61B 2034/715* (2016.02); *Y10S 901/29* (2013.01); *Y10S 901/30* (2013.01)

(58) Field of Classification Search
USPC ..................................................... 74/490.04
See application file for complete search history.

(56) References Cited

FOREIGN PATENT DOCUMENTS

| | | |
|---|---|---|
| JP | S56-116188 U | 9/1981 |
| JP | S59-134687 A | 8/1984 |
| JP | H11-48171 A | 2/1999 |
| JP | 2004-507370 A | 3/2004 |
| JP | 2009-136684 A | 6/2009 |
| JP | 2009-148557 A | 7/2009 |
| JP | 2009-160011 A | 7/2009 |
| JP | 2010-253162 A | 11/2010 |
| JP | 2012-143581 A | 8/2012 |
| JP | 2013-103137 A | 5/2013 |
| JP | 2013-514861 A | 5/2013 |
| JP | 2013-208506 A | 10/2013 |
| JP | 2014-57854 A | 4/2014 |
| JP | 2015-24032 A | 2/2015 |
| WO | 2012/166499 A1 | 12/2012 |

OTHER PUBLICATIONS

Jan. 9, 2018 International Preliminary Report on Patentability issued in International Patent Application No. PCT/JP2015/003484.

* cited by examiner

JOINT OF ROBOT ARM AND SURGICAL INSTRUMENT

TECHNICAL FIELD

The present invention relates to a joint of a robot arm and a surgical instrument configured by attaching a surgical tool to a tip end of the robot arm.

BACKGROUND ART

In recent years, endoscopic surgical operations (also called laparoscopic surgery) are attracting attention. Used in the endoscopic surgical operations is a surgical instrument configured by attaching a surgical tool to a tip end of a shaft. Examples of the surgical tool include forceps, graspers, scissors, staplers, needle holders, and electric scalpels. These surgical tools are used in accordance with contents of operations. In the endoscopic surgical operations, one or a plurality of holes are opened at, for example, an abdominal part of a patient, and a trocar is inserted as a passage port for tools. After that, a laparoscope and a surgical tool are inserted into a coelom through the trocar, and surgery for an affected part of the patient is performed. A surgeon monitors treatments by utilizing a monitor displaying an image of a surgical portion photographed by the laparoscope and operates the surgical instrument from an outside of the abdominal part.

Each of PTLs 1 and 2 shows this type of surgical instrument. A surgical instrument (medical manipulator) of PTL 1 includes: a connecting block; a distal-end working unit including a surgical tool; a shaft coupling the connecting block and the distal-end working unit to each other; and an actuator configured to drive the distal-end working unit by a wire. The shaft includes a first intermediate joint and a second intermediate joint. Each of the intermediate joints is formed such that a plurality of circular plate-shaped segments are stacked in a direction parallel to an axial direction of the shaft. The wire is inserted through the segments. The joints are bent by relaxing and tensing of the wire. Further, regarding three successive segments, a second segment is coupled to a first segment so as to be rotatable about a first axis perpendicular to the axial direction of the shaft, and a third segment is coupled to the second segment so as to be rotatable about a second axis that is perpendicular to the axial direction of the shaft and is different in phase by 90° from the first axis.

A surgical instrument (surgical device) of PTL 2 includes: a housing; a shaft extending from the housing; and an end effector provided at a tip end of the shaft. The shaft includes at least one articulating portion, and the articulating portion is formed by a plurality of joints which are nestingly arranged in series. Each of the plurality of joints includes a distal knuckle and a proximal clevis, and each knuckle operatively engages a clevis of an adjacent joint.

CITATION LIST

Patent Literature

PTL 1: Japanese Laid-Open Patent Application Publication No. 2009-160011
PTL 2: Japanese Laid-Open Patent Application Publication No. 2013-103137

SUMMARY OF INVENTION

Technical Problem

According to the shaft of PTL 1, the intermediate joints are bendable vertically and horizontally by a desired angle in a plane transverse to the shaft. However, since the bending of the joints is complex, control of the joints is also complex. Further, wires, cables, and the like which extend through insides of the joints and are not involved in bending and stretching of the joints are also relaxed or tensed in accordance with the bending and stretching of the joints.

According to the surgical device of PTL 2, a tip end of the knuckle of the joint is fitted in the clevis of the adjacent joint. With this, the joints adjacent to each other are separated from each other for securing operating ranges of these joints. However, the thickness of each joint is relatively large, and the plurality of joints just form, so to speak, a "bendable pipe." A bending radius of this bendable pipe is larger than, for example, a bending radius of a pin joint. To suppress the relaxing and tensing of the wires, cables, and the like, which extend through the insides of the joints and are not involved in the bending and stretching of the joints, at the time of the bending and stretching of the joints, it is desirable that: the bending radius of the joint be smaller, and a length of a center axis of the joint be constant regardless of the bending of the joint.

The present invention was made under these circumstances, and an object of the present invention is to solve at least one of problems of conventional arts.

Solution to Problem

A joint of a robot arm according to one aspect of the present invention is a joint of a robot arm, the joint coupling links of the robot arm to each other, the joint including: a plurality of plate-shaped segments lined up in a plate thickness direction; and an operating wire extending through the plurality of segments in the plate thickness direction at both first-direction sides of first-direction middle portions of the plurality of segments, the first direction being perpendicular to the plate thickness direction, wherein: a groove having a partially circular cross section and extending in a second direction perpendicular to the first direction is provided at a first-direction middle portion of one of two main surfaces of the adjacent segments, the two main surfaces facing each other in the plate thickness direction; a projection having a partially circular cross section and extending in the second direction is provided at a first-direction middle portion of the other of the two main surfaces; a curvature of a cross-sectional shape of the projection is larger than a curvature of a cross-sectional shape of the groove; the projection is fitted in the groove, and a bottom portion of the groove and a top portion of the projection contact each other; and a dimension of the projection in the plate thickness direction is larger than a dimension of the groove in the plate thickness direction and smaller than a length of a line connecting the bottom portion of the groove and an edge portion of the groove.

A surgical instrument according to one embodiment of the present invention includes: a robot arm including the joint of the above robot arm; and an end effector provided at a tip end of the robot arm.

According to the joint and the surgical instrument, since the curvature of the projection is larger than the curvature of the groove, a gap exists between the groove and the projection at both first-direction sides of the top portion of the projection. By utilizing this gap, one of the adjacent segments is rotatable relative to the other segment about the top portion of the projection. The joint bends and stretches by such relative rotations of the adjacent segments, and the contact between the bottom portion of the groove and the top portion of the projection is maintained regardless of the degree of the bending of the joint. Therefore, a change in the length of a line connecting contact points each between the adjacent segments of the plurality of segments in the plate thickness direction is small. Wires which are not involved in the bending and stretching of the joint are provided so as to overlap the above line. With this, the relaxing and tensing of the wires by the bending and stretching of the joint can be suppressed.

In addition to the above, the dimension of the projection in the plate thickness direction is larger than the dimension of the groove in the plate thickness direction, so that when the joint stretches, the edge portion of the groove does not contact the other main surface except for the projection. Further, the dimension of the projection in the plate thickness direction is smaller than the length of the line connecting the bottom portion of the groove and the edge portion of the groove, so that when the joint bends, the edge portion of the groove contacts the other main surface except for the projection, and the relative rotations of the adjacent segments are restricted. By such dimensional relation between the projection and the groove, while allowing the relative rotations of the adjacent segments, the facing main surfaces of the adjacent segments can be located close to each other in the plate thickness direction. Therefore, a larger number of segments can be arranged within a predetermined dimension of the joint in the plate thickness direction, and a bending radius of the joint can be made smaller.

Advantageous Effects of Invention

The present invention can provide a surgical instrument and a joint of a robot arm of the surgical instrument, by each of which at least one of problems of conventional arts is solved.

DESCRIPTION OF EMBODIMENTS

Figure 1:
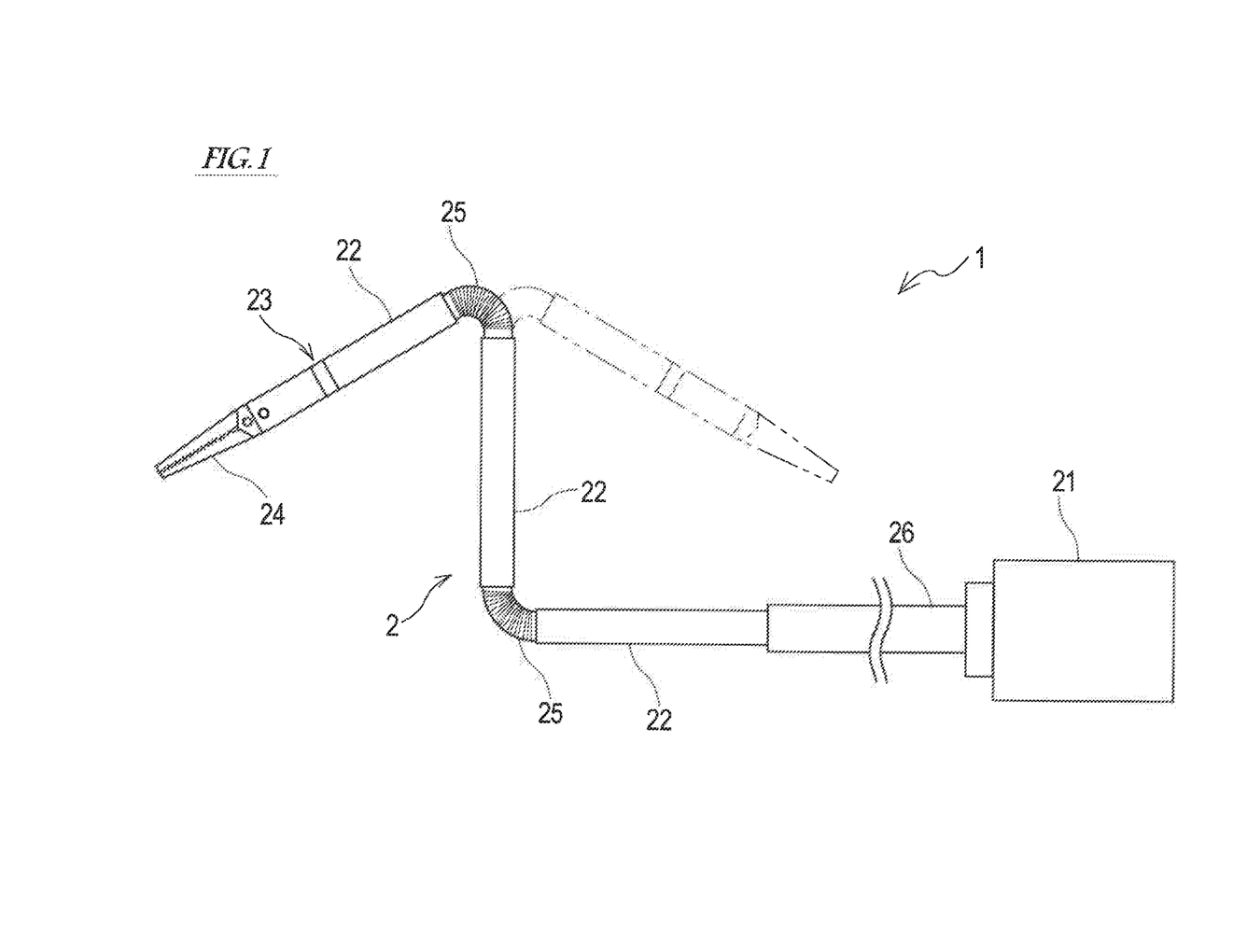
FIG. 1 is a diagram showing a schematic configuration of a surgical instrument according to one embodiment of the present invention.

Hereinafter, an embodiment of the present invention will be explained in reference to the drawings. FIG. 1 is a diagram showing a schematic configuration of a surgical instrument 1 according to one embodiment of the present invention. As shown in FIG. 1, the surgical instrument 1 is a so-called medical manipulator and includes: a robot arm 2 having a thin and long shaft shape; and an end effector 24 coupled to a tip end of the robot arm 2. The robot arm 2 includes: a base 21 provided at a base end of the robot arm 2; a wrist 23 provided at a tip end of the robot arm 2; a soft shaft 26 coupled to the base 21; a plurality of links 22 provided between the soft shaft 26 and the wrist 23; and joints 25 (one example of the joint of the robot arm 2 according to the present invention) coupling the plurality of links 22 to one another.

The base 21 is connected to a moving mechanism or a drive mechanism (both not shown). The soft shaft 26 is coupled to the base 21 so as to be rotatable. The soft shaft 26 has flexibility and a torque transmitting property of transmitting input torque to the link 22 located at the base end of the robot arm 2 among the plurality of links 22. The plurality of links 22 are hard tubular members, and wires and cables are inserted into insides of the links 22. The wrist 23 couples the end effector 24 to the link 22 located at the tip end of the robot arm 2 among the plurality of links 22 such that the end effector 24 is rotatable.

The end effector 24 denotes an actual operated portion which is inserted into a surgical portion of an abdominal cavity of a patient and can be driven from an outside of the abdominal cavity to execute a desired treatment or medical function with respect to a target tissue of the surgical portion. The end effector 24 may be a surgical tool such as forceps, a grasper, scissors, a stapler, a needle holder, or an electric scalpel. Or, the end effector 24 may be an electrically driven instrument, such as an electrosurgical electrode, a transducer, or a sensor. Or, the end effector 24 may be a suction nozzle, a gas injecting nozzle, a washing nozzle, a treatment fluid nozzle, an accessory introducing nozzle, or a nozzle through which a fluid for biopsy removal or the like is supplied. Or, the end effector 24 may be provided with an image pickup apparatus such as a camera.

The surgical instrument 1 denotes an instrument including the end effector 24. The surgical instrument 1 may be directly operated by a surgeon or may be operated by remote control by a remote surgical system using a robot or the like.

The joint 25 coupling the links 22 to each other will be explained in detail. The robot arm 2 according to the present embodiment includes two joints 25, and these joints 25 are similar in configuration to each other.

Figure 2:
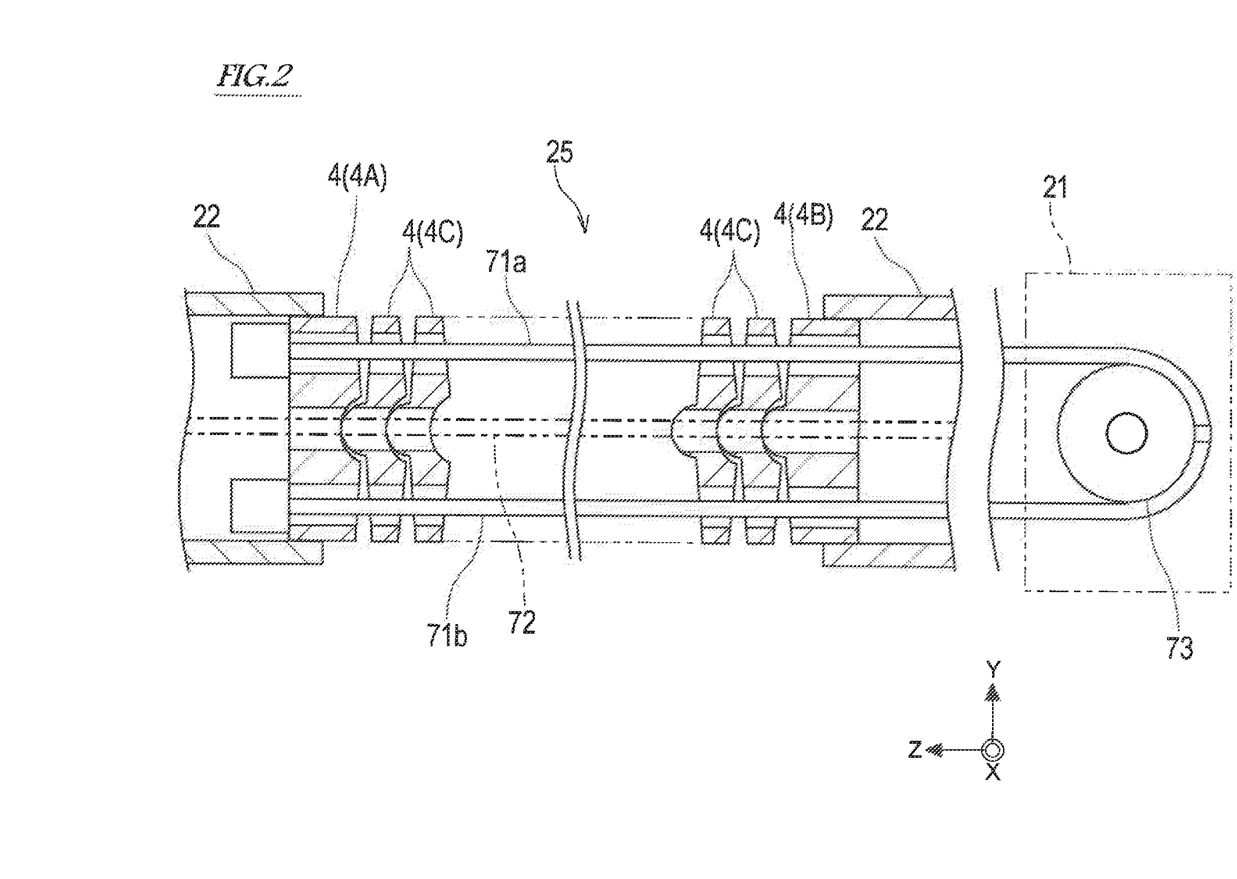
FIG. 2 is a sectional view showing a schematic configuration of a joint portion of a robot arm.

FIG. 2 is a sectional view showing a schematic configuration of the joint 25 of the robot arm 2 and shows the joint 25 in a stretched state. As shown in FIG. 2, the joint 25 is constituted by: a plurality of plate-shaped segments 4 lined up in series in a plate thickness direction Z; and at least one operating wire (71a, 71b) inserted through the plurality of segments 4 in the plate thickness direction Z.

The segment 4 located at one end among the plurality of segments 4 stacked in the plate thickness direction Z may be referred to as a first end segment 4A in order to distinguish it from the other segments 4. Further, the segment 4 located at the other end among the plurality of segments 4 stacked in the plate thickness direction Z may be referred to as a second end segment 4B in order to distinguish it from the other segments 4. Furthermore, the plurality of segments 4 located between the first end segment 4A and the second end segment 4B may be referred to as intermediate segments 4C in order to distinguish them from the first end segment 4A and the second end segment 4B. The first end segment 4A and the second end segment 4B are coupled to the respective links 22.

Figure 3A:
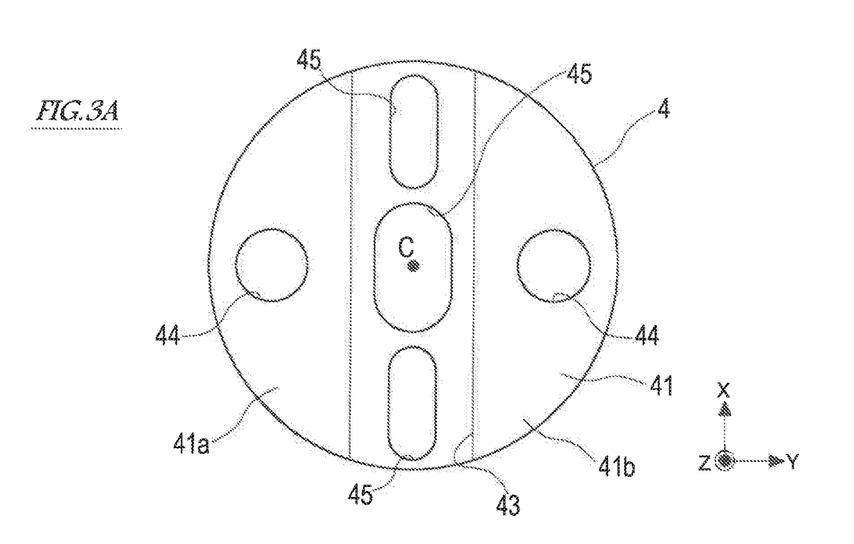
FIG. 3A is a diagram showing a segment when viewed from a plate thickness direction Z.
Figure 3B:
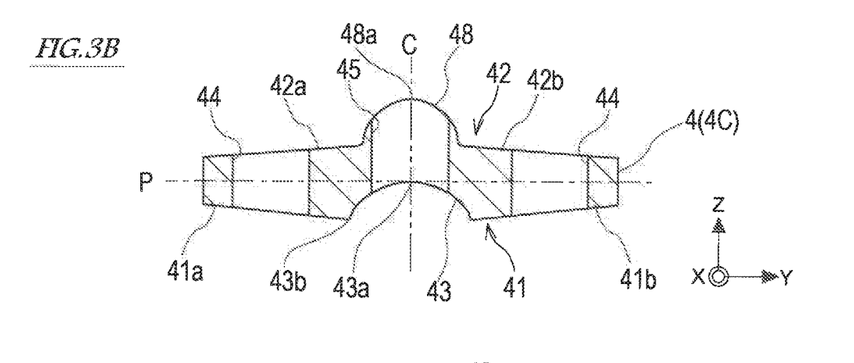
FIG. 3B is a sectional view including a center line of the segment (intermediate segment).

The configuration (shape) of the segment 4 will be explained in detail. FIG. 3A is a diagram showing the segment 4 when viewed from the plate thickness direction Z. FIG. 3B is a sectional view including a center line C of the segment 4 (intermediate segment 4C). Hereinafter, for convenience of explanation, a leftward/rightward direction on a paper surface of FIG. 3A is referred to as a "first direction Y," and a upward/downward direction on a paper surface of FIG. 3A is referred to as a "second direction X."

As shown in FIGS. 3A and 3B, the segment 4 has a substantially circular and thick plate shape and includes two main surfaces that are front and rear surfaces. Among the two main surfaces, a main surface facing one side in the plate thickness direction Z is referred to as a first surface 41, and a main surface facing the other side in the plate thickness direction Z is referred to as a second surface 42. A line passing through centers of the main surfaces 41 and 42 and parallel to the plate thickness direction Z is defined as the "center line C," and a virtual flat plane perpendicular to the center line C and parallel to the first direction Y and the second direction X is defined as a "reference plane P."

A groove 43 having a partially circular cross section is formed at a first-direction-Y middle portion of the first surface 41 of the segment 4. The groove 43 extends in the second direction X over an entire second-direction-X region of the first surface 41. To be specific, a dimension of the groove 43 in the second direction X and a dimension of the segment 4 in the second direction X are substantially equal to each other.

A projection 48 having a partially circular cross section is formed at a first-direction-Y middle portion of the second surface 42 of the segment 4. The projection 48 extends in the second direction X over an entire second-direction-X region of the second surface 42. To be specific, a dimension of the projection 48 in the second direction X and the dimension of the segment 4 in the second direction X are substantially equal to each other.

Further, the first surface 41 of the segment 4 is inclined relative to the reference plane P such that both first-direction-Y peripheral portions of the segment 4 are thinner than an edge portion of the groove 43, and the second surface 42 of the segment 4 is inclined relative to the reference plane P such that both first-direction-Y peripheral portions of the segment 4 are thinner than an edge portion of the projection 48. Especially, as shown in FIG. 3B, when the segment 4 is viewed from the second direction X, and the first surface 41 is virtually divided by the center line C into a half surface 41a located at one side in the first direction Y and a half surface 41b located at the other side in the first direction Y, both the half surface 41a and the half surface 41b are inclined relative to the reference plane P, and an inclination direction of the half surface 41a and an inclination direction of the half surface 41b are opposite to each other. Similarly, when the segment 4 is viewed from the second direction X, and the second surface 42 is virtually divided by the center line C into a half surface 42a located at one side in the first direction Y and a half surface 42b located at the other side in the first direction Y, both the half surface 42a and the half surface 42b are inclined relative to the reference plane P, and an inclination direction of the half surface 42a and an inclination direction of the half surface 42b are opposite to each other.

When the segment 4 is viewed from the second direction X, the inclination of the half surface 41a of the first surface 41 and the inclination of the half surface 41b of the first surface 41 are symmetrical about the center line C, and the inclination of the half surface 42a of the second surface 42 and the inclination of the half surface 42b of the second surface 42 are symmetrical about the center line C. As above, the segment 4 tapers from the edge portion of the groove 43 or the edge portion of the projection 48 toward the peripheral portions.

The segment 4 includes operation holes 44 which are located at both respective first-direction-Y sides of the groove 43 and the projection 48 and penetrate the segment 4 from the first surface 41 to the second surface 42. Each of the operation holes 44 is located at a second-direction-X middle portion of the segment 4.

The segment 4 is provided with at least one through hole 45 penetrating the segment 4. In the present embodiment, the segment 4 is provided with three through holes 45 lined up in the second direction X. The through holes 45 are provided at respective positions overlapping the groove 43 and the projection 48 and are open at a bottom portion of the groove 43 and a top portion of the projection 48.

Figure 4:
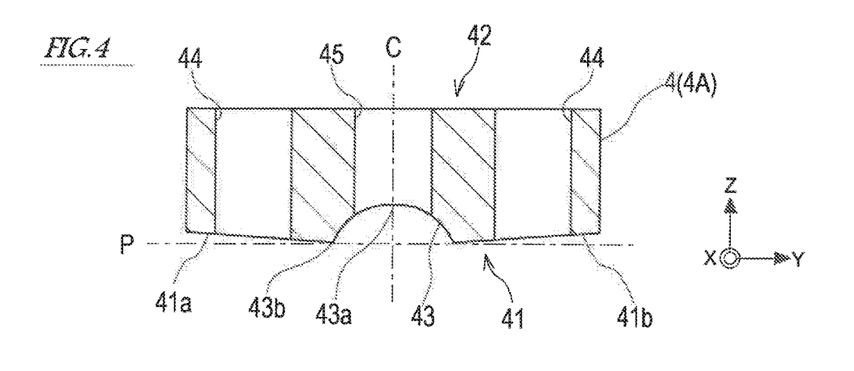
FIG. 4 is a sectional view including a center line of a first end segment.

FIG. 4 is a sectional view including the center line C of the first end segment 4A. The first end segment 4A is substantially the same in configuration (shape) as the segment 4 except that: the projection 48 is not provided on the second surface 42; and the second surface 42 is not inclined relative to the reference plane P (i.e., the second surface 42 is a flat surface parallel to the reference plane P).

Figure 5:
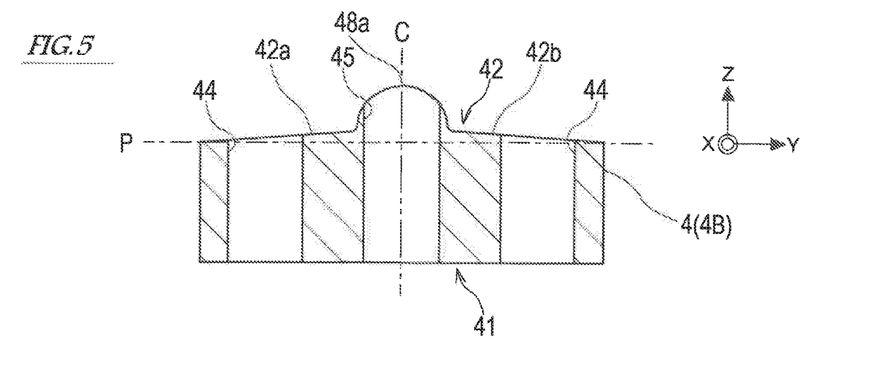
FIG. 5 is a sectional view including a center line of a second end segment.

FIG. 5 is a sectional view including the center line C of the second end segment 4B. The second end segment 4B is substantially the same in configuration (shape) as the segment 4 except that: the groove 43 is not provided on the first surface 41; and the first surface 41 is not inclined relative to the reference plane P (i.e., the first surface 41 is a flat surface parallel to the reference plane P).

Referring back to FIG. 2, the segments 4 are lined up in the plate thickness direction Z such that the projection 48 of one of the adjacent segments 4 is fitted in the groove 43 of the other segment 4.

The through holes 45 of the plurality of segments 4 lined up in the plate thickness direction Z as above communicate with one another, and wires 72 which are not involved in bending and stretching of the joint 25 are inserted through the through holes 45. For example, the wires 72 include: an operating wire for operating a movable portion, such as the joint (the wrist 23, for example) or the end effector 24, provided at the tip end side of the joint 25; and a wire extending to a device, such as a sensors or the end effector 24, provided at the tip end side of the joint 25.

The operation holes 44 of the plurality of segments 4 lined up in the plate thickness direction Z as above communicate with one another, and the operating wires 71a and 71b for operating the joint 25 are inserted through the operation holes 44.

One of end portions of each operating wire 71a, 71b is fixed to the first end segment 4A or a vicinity of the first end segment 4A. The other end portion of each operating wire 71a, 71b is fixed to a reel 73 provided at the base 21. It should be noted that these two operating wires 71a and 71b may be formed as a single wire configured by connecting these two wires 71a and 71b. By the operating wires 71a and 71b, the plurality of segments 4 lined up in the plate thickness direction Z are coupled to one another, and the adjacent segments are brought into pressure contact with each other in the plate thickness direction Z. When the reel 73 is rotated by a motor (not shown), one of the operating wires 71a and 71b is tensed, and the other is relaxed. Although the tensing and relaxing of the operating wires 71a and 71b are performed in conjunction with each other, the operating wires 71a and 71b may be configured to be independently operable.

Further, in the adjacent segments 4 among the plurality of segments 4 lined up in the plate thickness direction Z as above, the main surfaces 41 and 42 facing each other in the plate thickness direction Z have a predetermined dimensional relation. To be specific, a curvature of a cross-sectional shape of the projection 48 is larger than a curvature of a cross-sectional shape of the groove 43. Furthermore, a dimension of the projection 48 in the plate thickness direction Z is larger than a dimension of the groove 43 in the plate thickness direction Z and smaller than a line connecting a bottom portion 43a of the groove 43 and an edge portion 43b of the groove 43. Hereinafter, the predetermined dimensional relation between the projection 48 and the groove 43 will be specifically explained.

Figure 6:
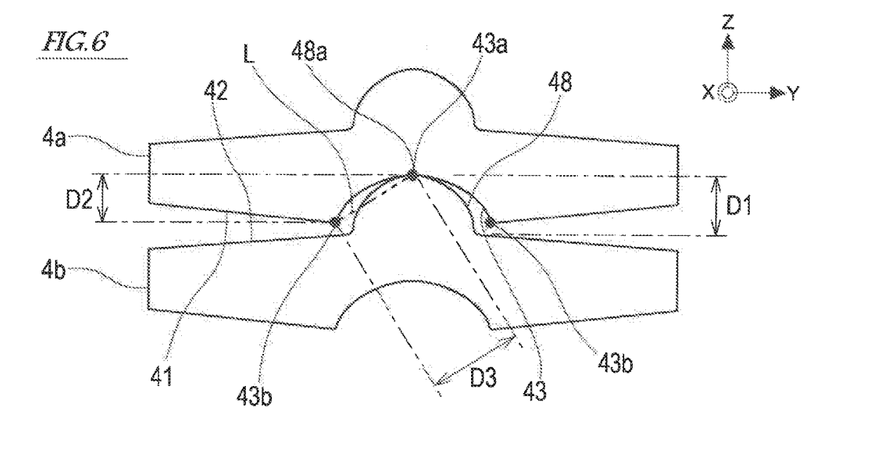
FIG. 6 is a diagram for explaining a dimensional relation between a projection and a groove.

FIG. 6 is a diagram for explaining the predetermined dimensional relation between the projection 48 and the groove 43. In FIG. 6, for simplicity, hatching of sections, the through holes 45, the operation holes 44, and the like are omitted. As shown in FIG. 6, in adjacent segments 4a and 4b, the two main surfaces 41 and 42 facing each other in the plate thickness direction Z includes the groove 43 and the projection 48, respectively. A curvature of a partial circle of a cross-sectional shape of the projection 48 is larger than a curvature of a partial circle of a cross-sectional shape of the groove 43. In other words, a curvature radius of the partial circle of the cross-sectional shape of the projection 48 is smaller than a curvature radius of the partial circle of the cross-sectional shape of the groove 43. Since the adjacent segments 4a and 4b are brought into pressure contact with each other in the plate thickness direction Z, a top portion 48a of the projection 48 fitted in the groove 43 contacts the bottom portion 43a of the groove 43. A gap is formed between the groove 43 and the projection 48 at both first-direction-Y sides of the top portion 48a of the projection 48. By utilizing this gap, the segment 4b is rotatable relative to the segment 4a about the top portion 48a of the projection 48 (about the bottom portion 43a of the groove 43). The joint 25 bends and stretches by such relative rotations of the adjacent segments 4a and 4b.

A dimension D1 of the projection 48 in the plate thickness direction Z is larger than a dimension D2 of the groove 43 in the plate thickness direction Z. With this, when the joint 25 stretches, the edge portion 43b of the groove 43 does not contact the second surface 42 of the segment 4b except for the projection 48, and the relative rotations of the adjacent segments 4a and 4b are allowed. It should be noted that: the dimension D1 of the projection 48 in the plate thickness direction Z denotes a size from the second surface 42 of the segment 4b to the top portion 48a of the projection 48 in the plate thickness direction Z; and the dimension D2 of the groove 43 in the plate thickness direction Z denotes a size from the first surface 41 of the segment 4a to the bottom portion 43a of the groove 43 in the plate thickness direction Z.

When the length of a line L connecting the bottom portion 43a of the groove 43 and the edge portion 43b of the groove 43 is represented by D3, the dimension D1 of the projection 48 in the plate thickness direction Z is smaller than the length D3. With this, when the joint 25 bends, the edge portion 43b of the groove 43 contacts the second surface 42 of the segment 4b except for the projection 48, and the relative rotations of the adjacent segments 4a and 4b are restricted.

As explained above, the surgical instrument 1 according to the present embodiment includes: the robot arm 2 including the joints 25; and the end effector 24 provided at the tip end of the robot arm 2.

The joint 25 of the robot arm 2 according to the present embodiment is the joint 25 coupling the links 22 of the robot arm 2 to each other and includes: the plurality of plate-shaped segments 4 lined up in the plate thickness direction Z; and the operating wires 71a and 71b located at both respective first-direction-Y sides of first-direction-Y middle portions of the plurality of segments 4 and extending through the plurality of segments 4 in the plate thickness direction Z. In the present embodiment, an outer shape of each segment 4 is a circular shape but is not limited to this and may be a rectangular shape, a circular shape, or the like.

In the adjacent segments 4 of the joint 25, the groove 43 extending in the second direction X and having the partially circular cross section is provided at the first-direction-Y middle portion of one (first surface 41) of the two main surfaces 41 and 42 facing each other in the plate thickness direction Z, and the projection 48 extending in the second direction X and having the partially circular cross section is provided at the first-direction-Y middle portion of the other (second surface 42) of the two main surfaces 41 and 42. The curvature of the cross-sectional shape of the projection 48 is larger than the curvature of the cross-sectional shape of the groove 43. The projection 48 is fitted in the groove 43, and the bottom portion 43a of the groove 43 and the top portion 48a of the projection 48 contact each other. The dimension D1 of the projection 48 in the plate thickness direction Z is larger than the dimension D2 of the groove 43 in the plate thickness direction Z and smaller than the length D3 of the line L connecting the bottom portion 43a of the groove 43 and the edge portion 43b of the groove 43.

According to the joint 25 configured as above, the joint 25 in a stretched state can be bent by tensing one of the operating wires 71a and 71b and relaxing the other. Further, the joint 25 in a bent state can be stretched by relaxing both the operating wires 71a and 71b. Since the joint 25 bends and stretches in a plane defined by the plate thickness direction Z and the second direction X, the control of the bending and stretching of the joint 25 and the control of the joint (the wrist 23, for example) and the end effector 24 provided at the tip end side of the joint 25 do not become complex. As in the surgical instrument 1 according to the present embodiment, when the robot arm 2 includes two or more joints 25, it is desirable that the joints 25 be configured to bend in the same plane. With this, the control of the bending and stretching of the joint 25 and the control of the joint and the end effector 24 provided at the tip end side of the joint 25 do not become complex.

According to the joint 25, since the curvature of the projection 48 is larger than the curvature of the groove 43, the gap exists between the groove 43 and the projection 48 at both first-direction-Y sides of the top portion 48*a* of the projection 48. By utilizing this gap, one of the adjacent segments 4 is rotatable relative to the other segment 4 about the top portion 48*a* of the projection 48. The joint 25 bends and stretches by the relative rotations of the adjacent segments 4, and the contact between the bottom portion 43*a* of the groove 43 and the top portion 48*a* of the projection 48 is maintained regardless of the degree of the bending of the joint 25. Therefore, a change in the length of a line (center axis of the joint 25) connecting contact points each between the adjacent segments 4 of the plurality of segments 4 in the plate thickness direction Z is small. To be specific, the center axis of the joint 25 is substantially constant regardless of the bending of the joint 25. The wires 72 which are not involved in the bending and stretching of the joint 25 are provided so as to overlap the above line. With this, the relaxing and tensing of the wires 72 by the bending and stretching of the joint 25 can be suppressed.

In addition to the above, the dimension D1 of the projection 48 in the plate thickness direction Z is larger than the dimension D2 of the groove 43 in the plate thickness direction Z, so that when the joint 25 stretches, the edge portion 43*b* of the groove 43 does not contact the second surface 42 except for the projection 48. Further, the dimension D1 of the projection 48 in the plate thickness direction Z is smaller than the length D3 of the line L connecting the bottom portion 43*a* of the groove 43 and the edge portion 43*b* of the groove 43, so that when the joint 25 bends, the edge portion 43*b* of the groove 43 contacts the second surface 42 except for the projection 48, and the relative rotations of the adjacent segments 4 are restricted. By such dimensional relation between the projection 48 and the groove 43, while allowing the relative rotations of the adjacent segments 4, the facing main surfaces 41 and 42 of the adjacent segments 4 can be located close to each other in the plate thickness direction Z.

According to the above dimensional relation between the projection 48 and the groove 43, a larger number of segments 4 can be arranged within a predetermined dimension of the joint 25 in the plate thickness direction Z. As the number of segments 4 within the predetermined dimension increases, a bent shape of the joint 25 becomes closer to a circular-arc shape. If the bent shape of the joint 25 becomes closer to the circular-arc shape, the bending of the joint 25 may be simplified to such an extent that the bending of the joint 25 can be controlled only by the rotation of the reel 73. In addition, by appropriately selecting the number of segments 4 within the predetermined dimension, the bending radius of the joint 25 can be made smaller. Thus, the joint 25 can be operated as not a "bendable pipe" but so to speak, a "pin joint."

Further, in the joint 25 according to the present embodiment, the through holes 45 of the plurality of segments 4 communicate with one another, and the wires 72 for the joints (the wrist 23, for example), the end effector 24, and the like provided at the tip end side of the joint 25 are inserted through the through holes 45. A length of a path formed by the through holes 45 for the wires 72 is not influenced by the bending and stretching of the joint 25 and changes little. Therefore, regarding the operations of the wires 72 for the joint, the end effector 24, and the like provided at the tip end side of the joint 25, it is unnecessary to consider the change in the length of the path by the bending and stretching of the joint 25. Therefore, it becomes easy to independently control the wrist 23 and the end effector 24. Further, the projection 48 and the groove 43 extend over the substantially entire second-direction-X region of the segment 4, and the through holes 45 can be provided in this region. Therefore, a larger number of wires 72 can be provided through the through holes 45.

In the present embodiment, on at least one of both first-direction-Y sides of the first-direction-Y middle portion of at least one of the plurality of segments 4, the thickness of the segment 4 gradually decreases from the edge portion of the groove 43 or the edge portion of the projection 48 toward a first-direction-Y end portion of the segment 4.

In the segment 4 according to the present embodiment, at least one of the first surface 41 and second surface 42 of the segment 4 is inclined relative to the first direction Y (reference plane P) such that on each of both first-direction-Y sides of the first-direction-Y middle portion of the segment 4, the thickness of the segment 4 gradually decreases from the edge portion of the groove 43 or the edge portion of the projection 48 toward the first-direction-Y peripheral portion of the segment 4.

Especially, on each of both first-direction-Y sides of the first-direction-Y middle portion of the intermediate segment 4C according to the present embodiment, the thickness of the intermediate segment 4C gradually decreases in a tapered manner from the edge portion of the groove 43 or the edge portion of the projection 48 toward the first-direction-Y peripheral portion of the intermediate segment 4C.

As above, since the segment 4 tapers on at least one of both first-direction-Y sides of the first-direction-Y middle portion of the segment 4, one of the adjacent segments 4 can be rotated relative to the other segment 4 toward a first-direction-Y side where the thickness tapers. A maximum bending angle of the joint 25 can be determined in accordance with the degree of the taper of the thickness of the segment 4.

In the surgical instrument 1 of the present embodiment, the robot arm 2 includes: the soft shaft 26 having the flexibility and the torque transmitting property; the wrist 23 coupled to the end effector 24; the plurality of links 22 provided between the soft shaft 26 and the wrist 23; and the joints 25 coupling the plurality of links 22 to one another.

In the surgical instrument 1, the joint 25 bends and stretches in a certain plane, but the link 22 can be rotated by the soft shaft 26 about the center axis of the link 22. As a result, the joint 25 can be bent in a desired direction at a desired angle, and the end effector 24 can be moved to a desired position in a three-dimensional space.

Modified Example 1

Figure 7:
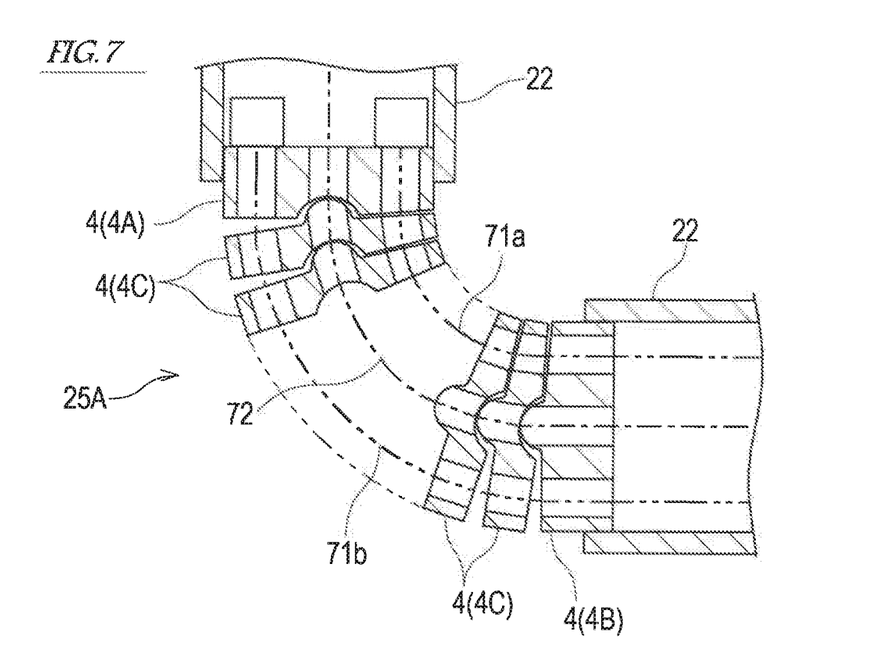
FIG. 7 is a sectional view showing a schematic configuration of a joint according to Modified Example 1.
Figure 8A:
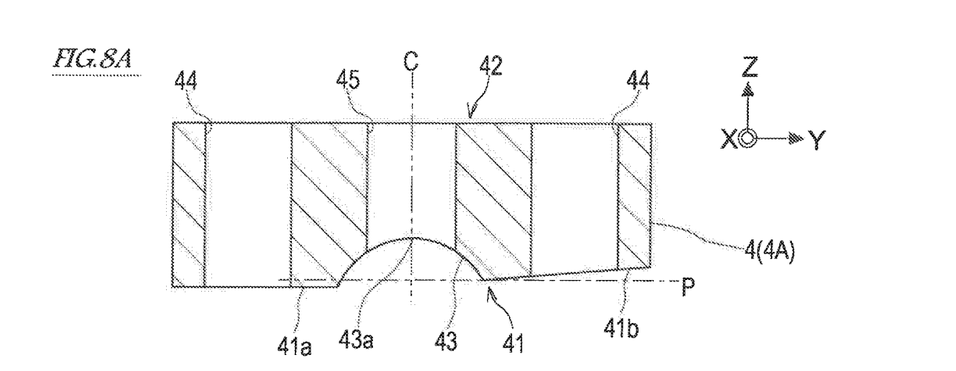
FIG. 8A is a sectional view including the center line of the first end segment of the joint according to Modified Example 1.
Figure 8B:
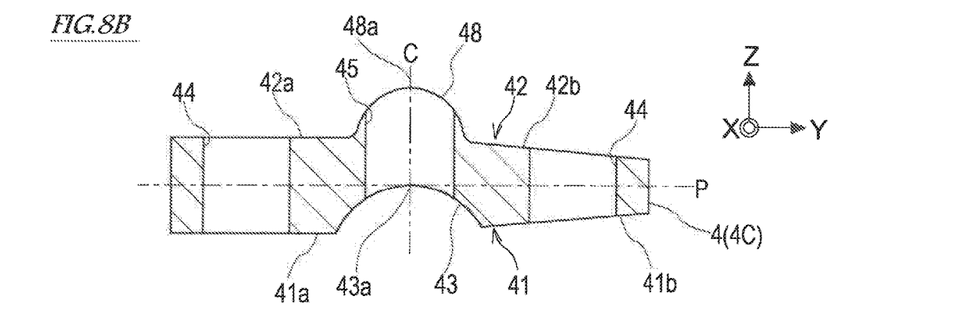
FIG. 8B is a sectional view including the center line of the segment (intermediate segment) of the joint according to Modified Example 1.
Figure 8C:
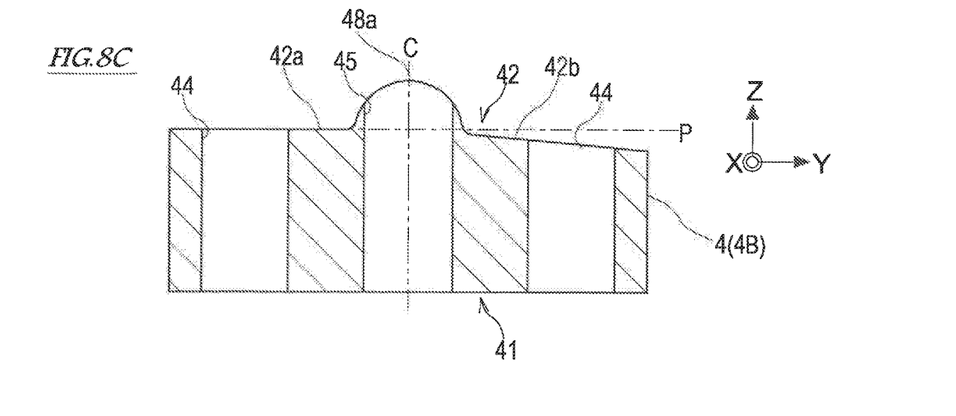
FIG. 8C is a sectional view including the center line of the second end segment of the joint according to Modified Example 1.

Next, Modified Example 1 of the joint 25 of the robot arm 2 of the surgical instrument 1 of the above embodiment will be explained. FIG. 7 is a sectional view showing a schematic configuration of a joint 25A of the robot arm 2 according to Modified Example 1. FIG. 8A is a sectional view including the center line C of the first end segment 4A of the joint 25A according to Modified Example 1 and defined by the plate thickness direction Z and the first direction Y. FIG. 8B is a sectional view including the center line C of the intermediate segment 4C of the joint 25A according to Modified Example 1 and defined by the plate thickness direction Z and the first direction Y. FIG. 8C is a sectional view including the center line C of the second end segment 4B of the joint according to Modified Example 1 and defined by the plate thickness direction Z and the first direction Y. In the explanations of the present modified example, the same reference signs are used for the same or corresponding members as the above embodiment, and a repetition of the same explanation may be avoided.

As shown in FIG. 1, in the above embodiment, the joint 25 is bendable toward both sides in the first direction Y. However, as shown in FIG. 7, the joint 25A according to Modified Example 1 is bendable toward only one side in the first direction Y. Unlike the joint 25 according to the above embodiment, the inclinations of the main surfaces 41 and 42 of the segment 4 of the joint 25A according to Modified Example 1 are different from each other. Hereinafter, the inclinations of the main surfaces 41 and 42 of the segment 4 will be explained in detail.

As shown in FIG. 8B, in the segment 4 (intermediate segment 4C) of the joint 25A according to Modified Example 1, the first surface 41 is divided by the center line C into the half surface 41b located at one side in the first direction Y and the half surface 41a located at the other side in the first direction Y, and the second surface 42 is divided by the center line C into the half surface 42b located at one side in the first direction Y and the half surface 42a located at the other side in the first direction Y. In this case, the half surface 41b and the half surface 42b are inclined relative to the first direction Y (reference plane P). With this, the thickness of a half of the segment 4 which half is located on one side of the center line C in the first direction Y tapers from the edge portion of the groove 43 or the edge portion of the projection 48 toward the first-direction-Y peripheral portion. Especially, the thickness of a half of the intermediate segment 4C which half is located on one side of the center line C in the first direction Y tapers from the edge portion of the groove 43 or the edge portion of the projection 48 toward the first-direction-Y peripheral portion.

As shown in FIG. 8A, the first end segment 4A of the joint 25A according to Modified Example 1 is substantially the same in configuration (shape) as the segment 4 except that: the projection 48 is not provided on the second surface 42; and the second surface 42 is not inclined relative to the reference plane P (i.e., the second surface 42 is a flat surface parallel to the reference plane P).

As shown in FIG. 8C, the second end segment 4B of the joint 25A according to Modified Example 1 is substantially the same in configuration (shape) as the segment 4 except that: the groove 43 is not provided on the first surface 41; and the first surface 41 is not inclined relative to the reference plane P (i.e., the first surface 41 is a flat surface parallel to the reference plane P).

In the joint 25A configured as above, on one first-direction-Y side of the first-direction-Y middle portion of the segment 4, the thickness of the joint 25A gradually decreases from the edge portion of the groove 43 or the edge portion of the projection 48 toward the first-direction-Y peripheral portion of the segment 4. Referring back to FIG. 7, the joint 25A configured as above is bendable toward only one side in the first direction Y about the top portion 48a of the projection 48 (about the bottom portion 43a of the groove 43). By limiting the degree of freedom of the bending of the joint 25A as above, a bending direction of the joint 25A can be stabilized, and the control of the joint 25A, and the joint and the end effector 24 provided at the tip end side of the joint 25A can be simplified.

Modified Example 2

Figure 9:
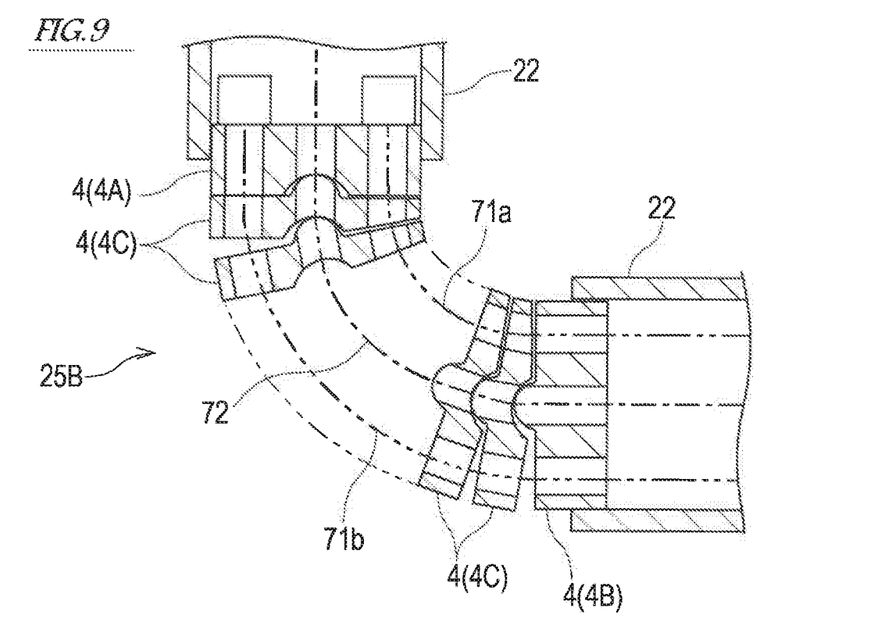
FIG. 9 is a sectional view showing a schematic configuration of the joint according to Modified Example 2.
Figure 10A:
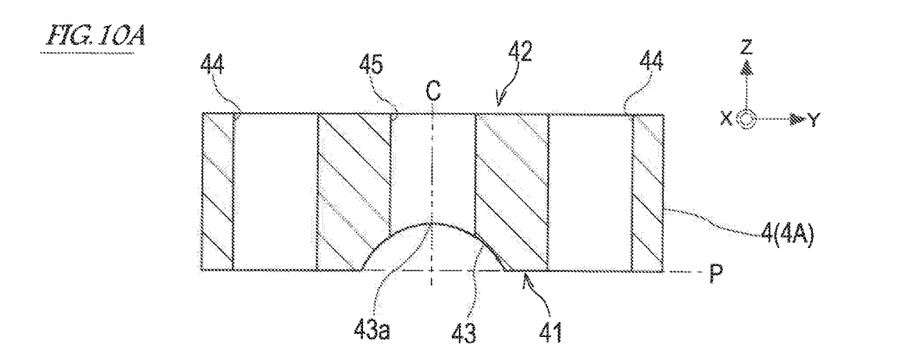
FIG. 10A is a sectional view including the center line of the first end segment of the joint according to Modified Example 2.
Figure 10B:
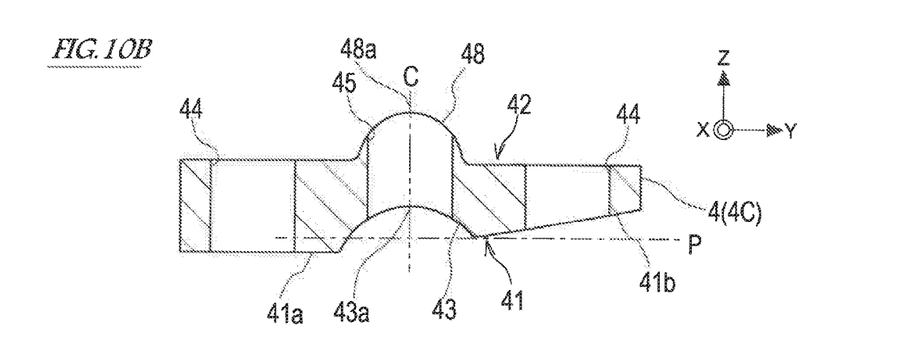
FIG. 10B is a sectional view including the center line of the segment (intermediate segment) of the joint according to Modified Example 2.
Figure 10C:
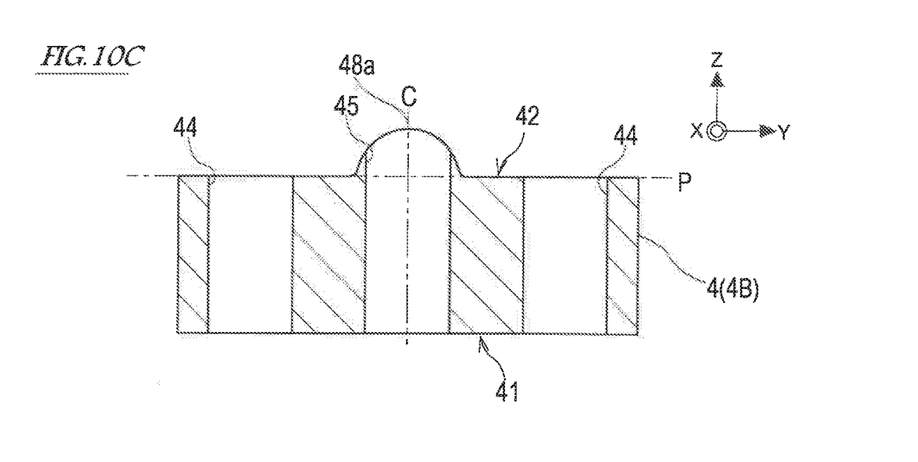
FIG. 10C is a sectional view including the center line of the second end segment of the joint according to Modified Example 2.

Next, Modified Example 2 of the joint 25 of the robot arm 2 of the surgical instrument 1 of the above embodiment will be explained. FIG. 9 is a sectional view showing a schematic configuration of the joint 25B of the robot arm 2 according to Modified Example 2. FIG. 10A is a sectional view including the center line C of the first end segment 4A of the joint 25B according to Modified Example 2 and defined by the plate thickness direction Z and the first direction Y. FIG. 10B is a sectional view including the center line C of the segment 4 (intermediate segment 4C) of the joint 25B according to Modified Example 1 and defined by the plate thickness direction Z and the first direction Y. FIG. 10C is a sectional view including the center line C of the second end segment 4B of the joint 25B according to Modified Example 1 and defined by the plate thickness direction Z and the first direction Y. In the explanations of the present modified example, the same reference signs are used for the same or corresponding members as the above embodiment, and a repetition of the same explanation may be avoided.

As shown in FIG. 1, in the above embodiment, the joint 25 is bendable toward both sides in the first direction Y. However, as shown in FIG. 9, the joint 25B according to Modified Example 2 is bendable toward only one side in the first direction Y. The inclinations of the main surfaces 41 and 42 of each segment 4 of the joint 25B according to Modified Example 2 are different from the inclinations of the main surfaces 41 and 42 of each segment 4 of the joint 25 according to the above embodiment. Hereinafter, the inclinations of the main surfaces 41 and 42 of each segment 4 of the joint 25B will be explained in detail.

As shown in FIG. 10B, in the segment 4 (intermediate segment 4C) of the joint 25B according to Modified Example 2, the first surface 41 is divided by the center line C into the half surface 41b located at one side in the first direction Y and the half surface 41a located at the other side in the first direction Y. In this case, only the half surface 41b of the first surface 41 is inclined relative to the first direction Y (reference plane P). With this, the thickness of a half of the intermediate segment 4C which half is located on one side of the center line C in the first direction Y tapers from the edge portion of the groove 43 or the edge portion of the projection 48 toward the first-direction-Y peripheral portion. It should be noted that: the second surface 42 of the segment 4 is parallel to the reference plane P; and the second surface 42 is not substantially inclined.

As shown in FIG. 10A, the first end segment 4A of the joint 25B according to Modified Example 2 is substantially the same in configuration (shape) as the segment 4 except that: the projection 48 is not provided on the second surface 42; and the first surface 41 is not inclined relative to the reference plane P (i.e., the first surface 41 is a flat surface parallel to the reference plane P).

As shown in FIG. 10C, the second end segment 4B of the joint 25B according to Modified Example 2 is substantially the same in configuration (shape) as the segment 4 except that: the groove 43 is not provided on the first surface 41; and the first surface 41 is not inclined relative to the reference plane P (i.e., the first surface 41 is a flat surface parallel to the reference plane P).

In the joint 25B configured as above, on one first-direction-Y side of the first-direction-Y middle portion of the intermediate segment 4C, only one of the main surfaces of the intermediate segment 4C is inclined relative to the first direction Y. Referring back to FIG. 9, the joint 25B configured as above is bendable toward only one side in the first direction Y about the top portion 48a of the projection 48 (about the bottom portion 43a of the groove 43). By limiting the degree of freedom of the bending of the joint 25B as above, a bending direction of the joint 25B can be stabilized, and the control of the joint 25B, and the joint and the end effector 24 provided at the tip end side of the joint 25B can be simplified.

The foregoing has explained the preferred embodiment (and the modified examples) of the present invention. From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the scope of the present invention.

REFERENCE SIGNS LIST 1 surgical instrument
2 robot arm
4 segment
4A first end segment
4B second end segment
4C intermediate segment
21 base
22 link
23 wrist
24 end effector
25, 25A, 25B joint
26 soft shaft
41, 42 main surface
43 groove
43a bottom portion
43b edge portion
44 operation hole
through hole
48 projection
48a top portion
71a, 71b operating wire
72 wires
C center line

The invention claimed is:

1. A joint of a robot arm, the joint coupling links of the robot arm to each other,
the joint comprising:
a plurality of plate-shaped segments lined up in a plate thickness direction, each of the plurality of segments having a first-direction middle portion positioned at a middle of the segment in a first direction perpendicular to the plate thickness direction; and
an operating wire extending through the plurality of segments in the plate thickness direction at sides of the first-direction middle portion of each of the plurality of segments, the sides being opposed to each other in the first direction, wherein:
a groove having a partially circular cross section and extending in a second direction perpendicular to the first direction is provided at a main surface of the first-direction middle portion of a first of the plurality of segments;
a projection having a partially circular cross section and extending in the second direction is provided at a main surface of the first-direction middle portion of a second of the plurality of segments, the first and second segments being adjacent to each other and the main surfaces facing each other in the plate-thickness direction;
a curvature of a cross-sectional shape of the projection is larger than a curvature of a cross-sectional shape of the groove;
the projection is fitted in the groove, and a bottom portion of the groove and a top portion of the projection contact each other; and
a dimension of the projection in the plate thickness direction is larger than a dimension of the groove in the plate thickness direction and smaller than a length of a line connecting the bottom portion of the groove and an edge portion of the groove.

2. The joint according to claim 1, wherein each of the plurality of segments includes a through hole extending through the groove and projection of the segment and penetrating the segment in the plate thickness direction.

3. The joint according to claim 1, wherein a dimension of the grooves and projections of the plurality of segments in the second direction and a dimension of the plurality of segments in the second direction are substantially equal to each other.

4. The joint according to claim 1, wherein on at least one of the first-direction sides of the first-direction middle portion of at least one of the plurality of segments, a thickness of the at least one segment decreases from the edge portion of the groove or an edge portion of the projection toward a first-direction end portion of the at least one segment.

5. The joint according to claim 1, wherein on at least one of the first-direction sides of the first-direction middle portion of at least one of the plurality of segments, a thickness of the at least one segment decreases in a tapered manner from the edge portion of the groove or an edge portion of the projection toward a first-direction end portion of the at least one segment.

6. A surgical instrument comprising:
a robot arm including the joint according to claim 1; and
an end effector provided at a tip end of the robot arm.

7. The surgical instrument according to claim 6, wherein the robot arm includes:
a soft shaft having flexibility and a torque transmitting property;
a wrist coupled to the end effector;
a plurality of links provided between the soft shaft and the wrist; and
the joint coupling the plurality of links to each other.

* * * * *